United States Patent [19]

Berndt

[11] Patent Number: 5,705,384
[45] Date of Patent: Jan. 6, 1998

[54] COMPACT HIGH-VOLUME MICROORGANISM DETECTION APPARATUS

[75] Inventor: Klaus W. Berndt, Stewartstown, Pa.

[73] Assignee: Becton Dickinson and Company, Franklin Lakes, N.J.

[21] Appl. No.: 648,798

[22] Filed: May 16, 1996

[51] Int. Cl.⁶ .................. C12M 3/00; G01N 21/00; G01N 21/90
[52] U.S. Cl. .................. 435/286.2; 435/286.7; 435/287.3; 435/288.7; 422/64; 422/82.05; 422/82.08; 356/427
[58] Field of Search .................. 435/286.1, 286.2, 435/286.7, 287.3, 288.7, 303.1; 422/64, 82.05, 82.08; 356/39, 427, 435

[56] References Cited

U.S. PATENT DOCUMENTS

| | | | |
|---|---|---|---|
| 4,576,916 | 3/1986 | Lowke et al. | 435/289 |
| 5,371,016 | 12/1994 | Berndt | 435/291 |
| 5,397,709 | 3/1995 | Berndt | 436/34 |
| 5,473,437 | 12/1995 | Blumenfeld et al. | 356/417 |
| 5,498,543 | 3/1996 | Berndt | 435/286.1 |

Primary Examiner—David A. Redding
Attorney, Agent, or Firm—Alan W. Fiedler

[57] ABSTRACT

The present invention describes an automated compact high-volume microorganism detection apparatus for detecting microorganisms in a large number of sample containers. The containers are placed in a plurality of vessels that hang vertically on horizontal rods mounted to the circumference of a cylindrical spool that is rotated around a horizontal shaft. During rotation of the spool, the vessels can remain vertically oriented or can be tilted by an arbitrary angle, before they fall back into their original vertical orientation. Depending on the percentage of tilt selected, sample agitation will be absent, soft, or more vigorous.

12 Claims, 12 Drawing Sheets

COMPACT HIGH-VOLUME MICROORGANISM DETECTION APPARATUS

BACKGROUND OF THE INVENTION

1. Field of the Invention

The present invention relates to an automated compact high-volume microorganism detection apparatus.

2. Background Description

The presence of biologically active agents such as bacteria in a patient's body fluid, especially blood, is generally determined using blood culture vials. A small quantity of blood is injected through an enclosing rubber septum into a sterile vial containing a culture medium, and the vial is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different vials. It has also been proposed to detect microorganism growth in sealable containers by monitoring positive and/or negative pressure changes.

Recently, non-invasive methods have been developed involving chemical sensors disposed inside the vial. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each vial. This results in station sensitivity variations from one vial to the next. Therefore, extensive and time-consuming calibration procedures are required to operate such systems. In addition, flexible electrical cables are required to connect the individual sources and detectors with the rest of the instrument. With the large number of light sources, typically 240 or more per instrument, maintenance can become very cumbersome and expensive when individual sources start to fail.

In known colorimetric or fluorometric instruments, light emitting diodes ("LEDs") are used as the individual light sources. These sources have only a relatively low optical output power. Therefore, high photometric detection sensitivity is required to monitor the vial sensor emissions. This results in additional and more complicated front-end electronics for each photodetector, increasing production cost. To reduce equipment cost and complexity, it has been proposed to use optical fibers at each vial to feed the output light of an instrument's sensors to a central photodetector. A disadvantage to this approach is the need for arranging a large number of relatively long fibers of different length within the instrument.

SUMMARY OF THE INVENTION

The present invention overcomes the above problems and comprises an automated compact high-volume microorganism detection apparatus. The present invention is, in particular, advantageous in connection with small-size sample containers as used in the field of tuberculosis testing. A typical small-size sample container is the Mycobacterial Growth Indicator Tube (MGIT) which is produced by Becton Dickinson Microbiology Systems, Cockeysville, Md.

It is an objective of the present invention to provide a microorganism detection apparatus that can accommodate a large number of sample containers, has a small footprint, can be produced at low cost, works reliable over extended time intervals, allows for individual sample identification, offers simultaneous access to a large number of samples during loading and unloading, and allows variation of the degree of agitation of the sample containers.

According to the present invention, the above objective is achieved by arranging the sample tubes vertically side by side in a number of long vessels that hang vertically on horizontal rods mounted to the circumference of a cylindrical spool that is rotated around a horizontal shaft. During rotation of the spool, the vessels remain vertically oriented. In this way, any sample agitation can be avoided, if required for biological reasons.

It is also possible to lock the vessels to the spool for a certain percentage of a spool rotation period. This feature allows the sample tubes to be tilted by an arbitrary angle, before they fall back into their original vertical orientation. Depending on the percentage selected, sample agitation will be absent, soft, or more vigorous. In other words, an apparatus according to the present invention provides means to optimize the frequency and the degree of sample agitation according to the biological requirements.

The vessels accommodate two rows of sample tubes each in its own chamber. In the long vessel walls there are windows that allow access to barcode labels attached to each sample tube. Two barcode readers are arranged on a carriage that can be moved parallel to the spool shaft on rails mounted to the apparatus mainframe below the spool. For barcode reading, spool rotation is interrupted and the carriage is moved across the whole length of the spool. In this way, two rows of sample containers are scanned. In a next step, the spool is rotated by an appropriate angle, and the carriage is moved again across the whole spool length. This procedure is repeated until all sample tubes are scanned.

Within the vessel bottoms, there are also two rows of openings to allow for interrogating bacterial sensors that are attached to the inner bottom of each sample tube. A bacterial sensor reading head is mounted to the same carriage that holds the two barcode readers. The bacterial sensor reading head is constructed so that it can access two adjacent sample tubes, i.e., one in each row, simultaneously. In order to interrogate a particular vessel, the spool is rotated into the appropriate angular position and the carriage is moved across the whole spool length. This procedure is repeated until the sample tubes in all vessels within the apparatus are read.

Each vessel can be as long as the spool and can be mounted permanently to the horizontal rods. It is also possible to segment the vessels into appropriate lengths so that the number of sample tubes within one vessel matches with particular requirements for antimicrobic susceptibility testing (AST). In this case, it may be more convenient if the vessels can be removed from the rods, and re-inserted after loading a new group of test samples.

These and other aspects, features and advantages of the present invention will become apparent from the following detailed description, taken in conjunction with the accompanying drawings.

DETAILED DESCRIPTION

Figure 1:
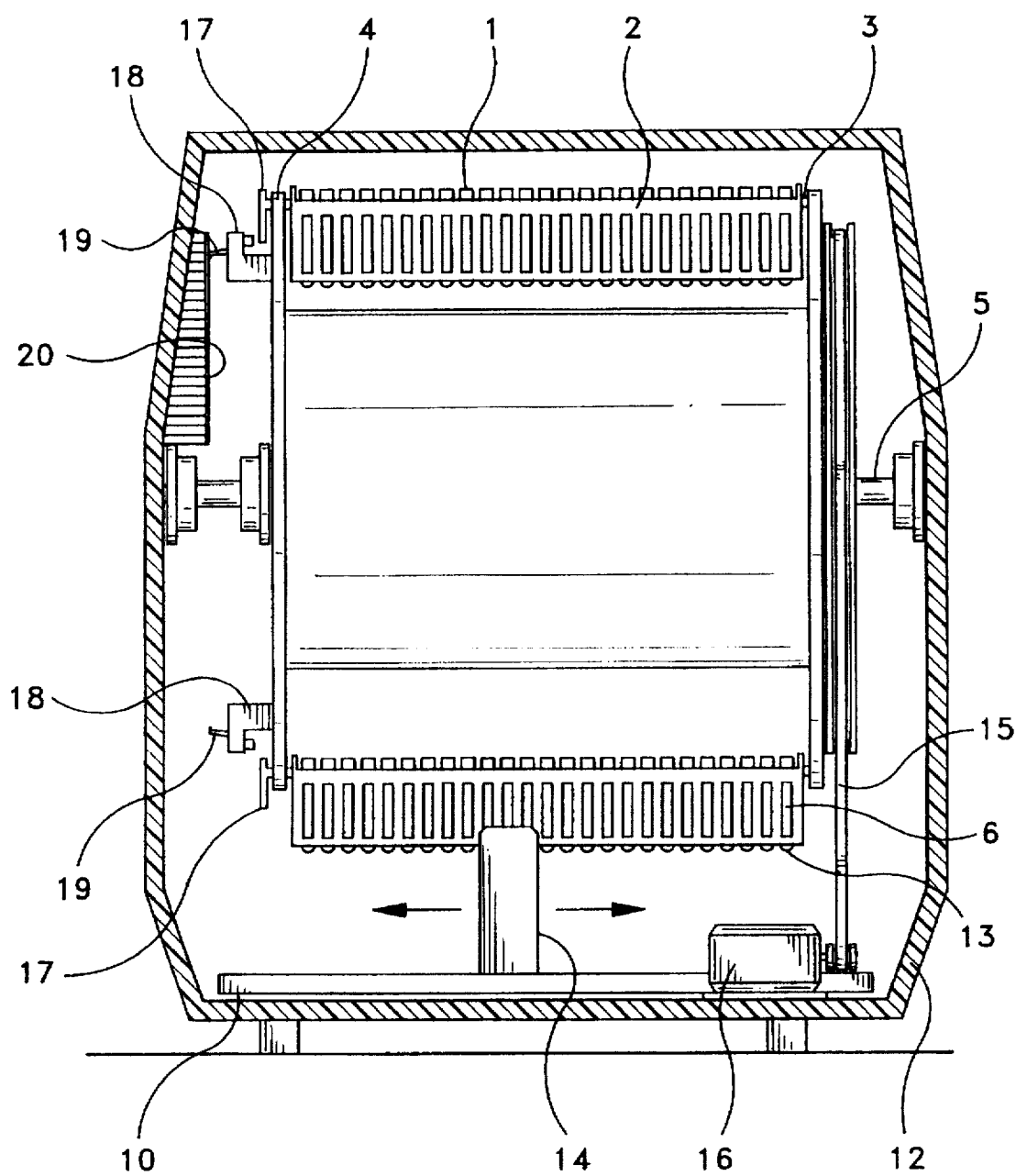
FIG. 1 shows a front view of the interior of a compact high-volume microorganism detection apparatus according to the present invention with vessels containing two rows of sample tubes, with 25 sample tubes per row.

According to the present invention, a multitude of sample tubes 1 is vertically oriented side by side in a number of long vessels 2 that are hanging vertically on horizontal rods 3 mounted to the circumference of a cylindrical spool 4 that is rotating around a horizontal shaft 5. During rotation of spool 4, the vessels 2 remain vertically oriented. In this way, any sample agitation can be avoided, if required for biological reasons.

An apparatus according to the present invention can accommodate up to 800 Mycobacterial Growth Indicator Tubes (MGIT) which are produced by Becton Dickinson Microbiology Systems. The apparatus has a small size of only 35"×"×37" (W×D×H). The machine structure is simple and the number of parts is relatively low, so that the system can be produced at low cost, has a long meantime between failures (MTBF) and a short time to repair. The construction allows for simultaneous access to approximately 150 tubes for the purpose of loading and unloading. The system provides for barcode reading on each tube 1 after loading them into the apparatus. The frequency and the intensity of sample container agitation can be controlled via software according to the biological requirements. Due to the fact that only one bacterial sensor head 14 is required to interrogate all 800 tubes, a sophisticated time-resolved fluorescence detection technology can be applied, which results in excellent long-time stability and maximum sensor resolution. Therefore, an apparatus according to the present invention offers a good chance to shorten the time to detection, and is suitable to perform not only detection, but also antimicrobial susceptibility testing (AST).

Variable agitation is provided by the apparatus locking vessels 2 to spool 4 for a certain percentage of a spool rotation period. This feature allows sample tubes 1 to be tilted by an arbitrary angle, before they fall back into their originally vertical orientation. Depending on the percentage selected, the sample agitation will be absent, soft, or more vigorous. In other words, an apparatus according to the present invention provides means to optimize the frequency and the degree of sample agitation according to the biological requirements.

Figure 6:
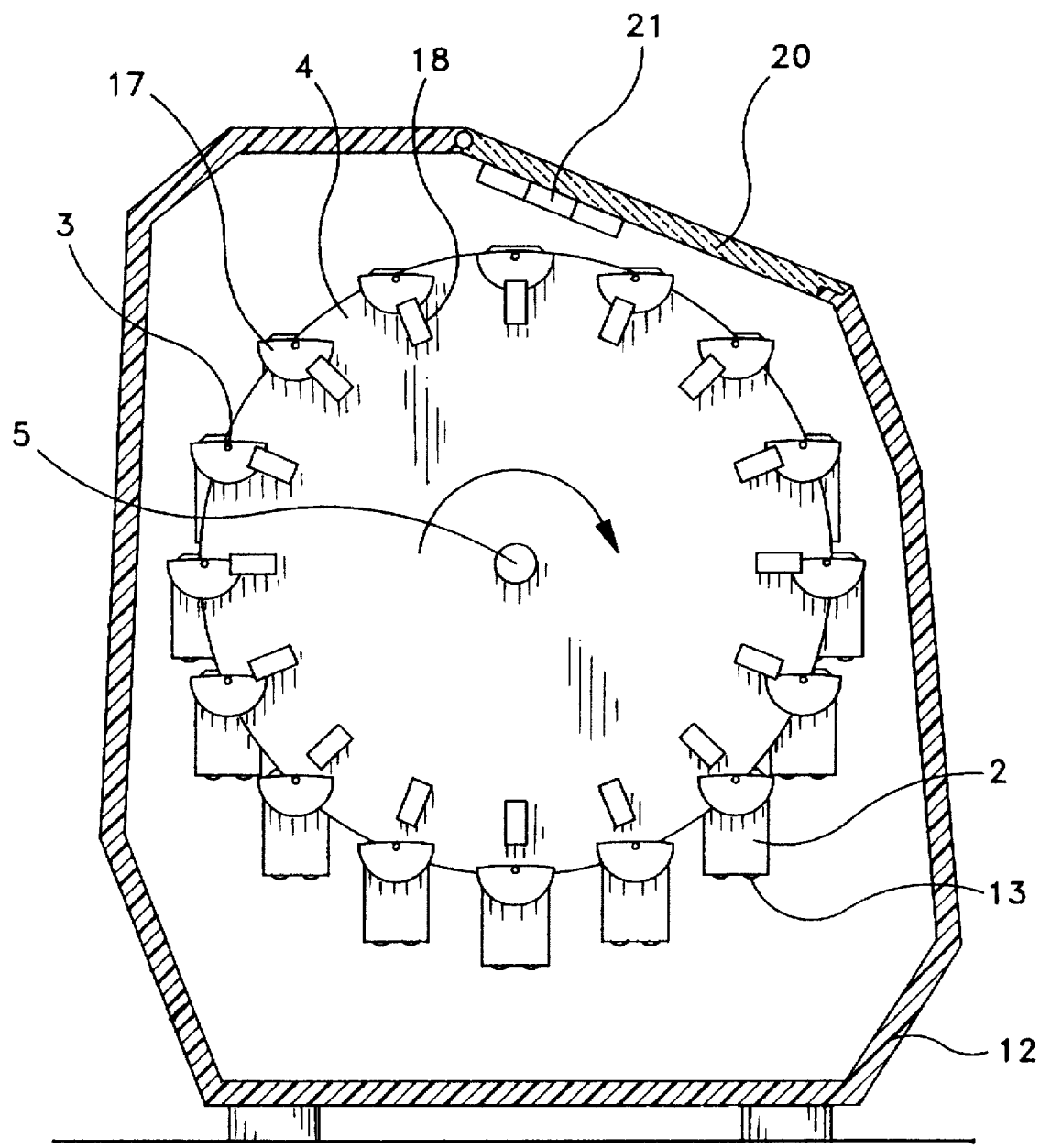
FIG. 6 shows another side view of the interior of the apparatus shown in FIG. 1 and a locking mechanism for the vessels.
Figure 7:
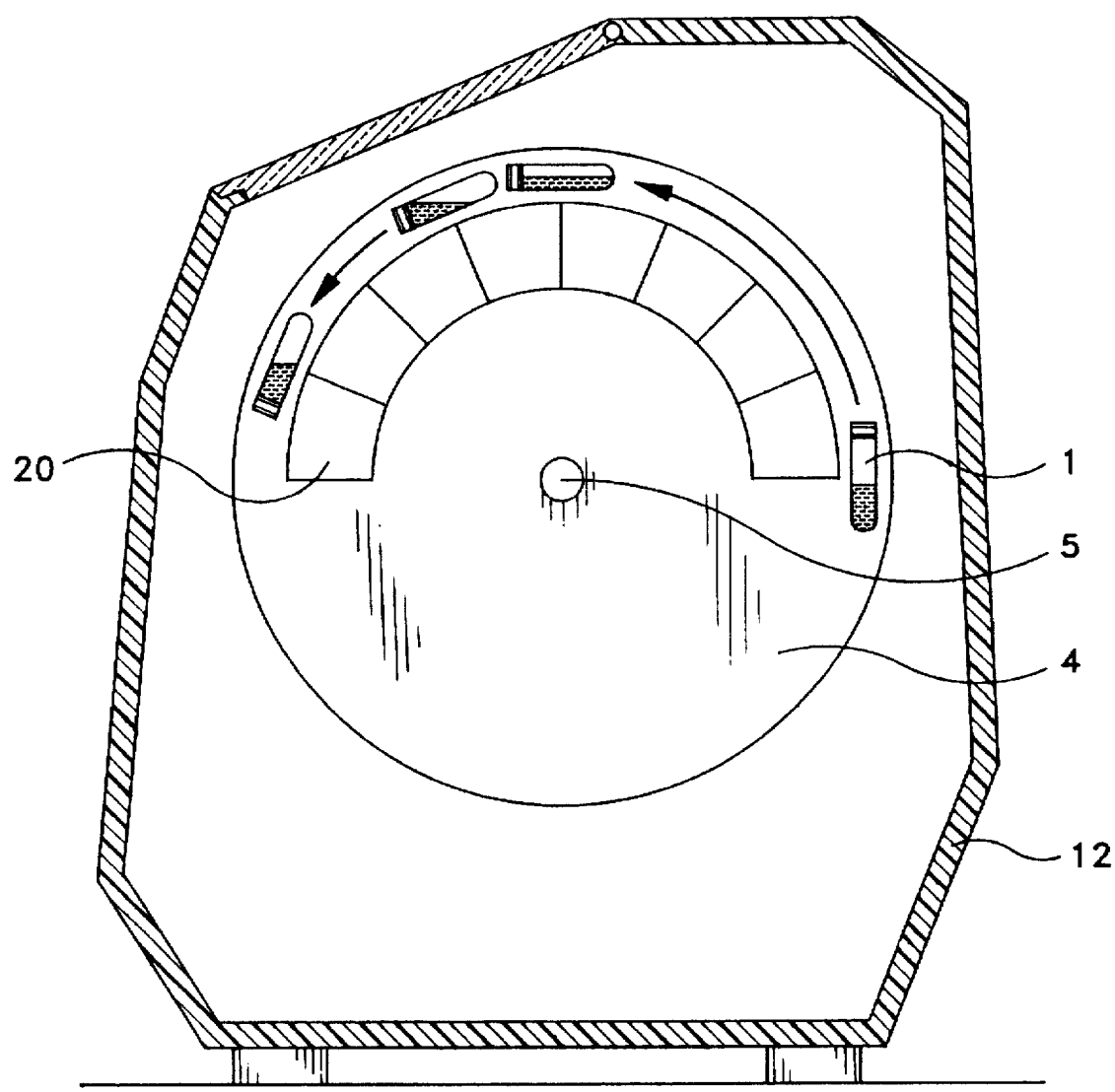
FIG. 7 shows a side view of the interior of the apparatus shown in FIG. 1 and the different possible degrees of tilting of the sample tubes during spool rotation.

Controlling the degree of agitation is achieved by using electro-magnets 18, half-moon-shaped metallic disks 17, brushes 19 and a segmented electrode array 20, all shown in FIGS. 1, 6, and 7. Each of the horizontal rods 3 carries on one end a half-moon-shaped metallic disk 17. One electro-magnet 18 is mounted onto each end of spool 4 around the spool's radius between shaft 5 and each horizontal rod 3, as illustrated in FIG. 6. Segmented electrode array 20 is mounted on an internal wall of a thermo-isolated housing 12 such that brushes 19 make contact with segments of the electrode array 20 during spool rotation, as discussed below.

In operation, a system controller computer powers a selected number of electrode segments of array 20 with a voltage. If, during spool rotation, a particular vessel 2 approaches a first electrode segment area and the segment is powered by the system controller, then the corresponding electro-magnet 18 will receive electrical power via brush 19 from that segment, and will lock the corresponding half-moon-shaped disk 17 to spool 4. This means that the corresponding vessel 2 will be tilted during further spool rotation. The degree of tilting depends on how many electrode segments are powered by the system controller. This is illustrated in FIG. 7, which shows different tilting orientations of a sample tube 1. If the vessel reaches a position where the corresponding electrode segment is not receiving electrical power, electro-magnet 18 becomes deactivated, and vessel 2 falls back into its original vertical orientation.

Figure 4:
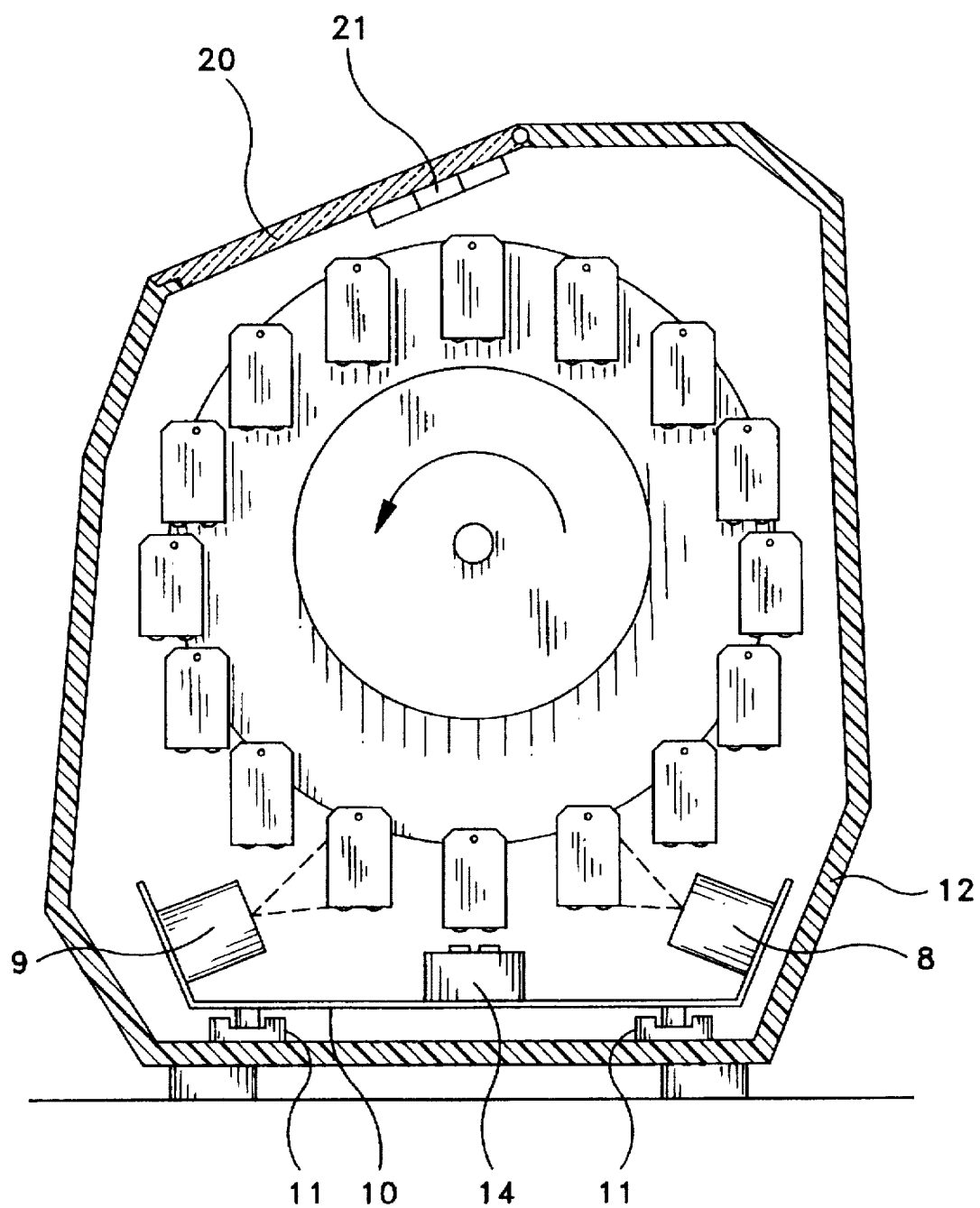
FIG. 4 shows a side view of the interior of the compact high-volume microorganism detection apparatus, shown in FIG. 1, with 16 vessels each containing two rows of sample tubes.
Figure 5:
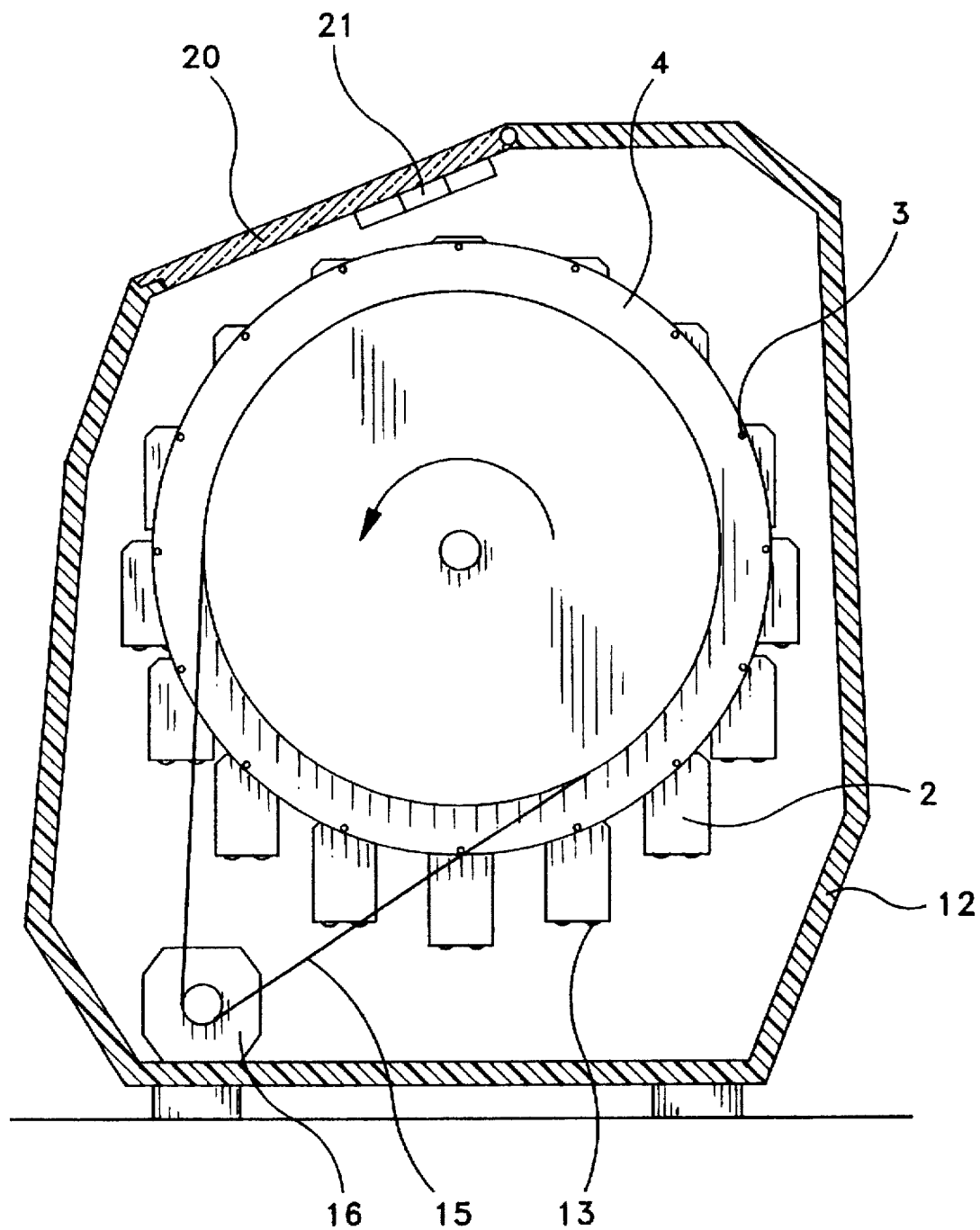
FIG. 5 shows another side view of the interior of the apparatus shown in FIG. 1 and a driving mechanism for the spool.

As shown in FIGS. 1 and 5, spool 4 is driven by a motor 16 via belt 15. Preferably, motor 16 is a stepper motor so that spool 4 can either rotate continuously or can be stopped in any required position. Spool 4 is arranged and rotatably mounted in thermo-isolated housing 12 as shown in FIGS. 1, 4, 5, 6, 7, and 10. Housing 12 is equipped with a door 20, as shown in FIG. 4, to allow for sample loading and un-loading. Door 20 can carry an indicator array 21 depicting the position number of positive sample tubes and other information. The interior of housing 12 is temperature-stabilized at approximately 35° C. to allow for optimum growth conditions.

Figure 2:
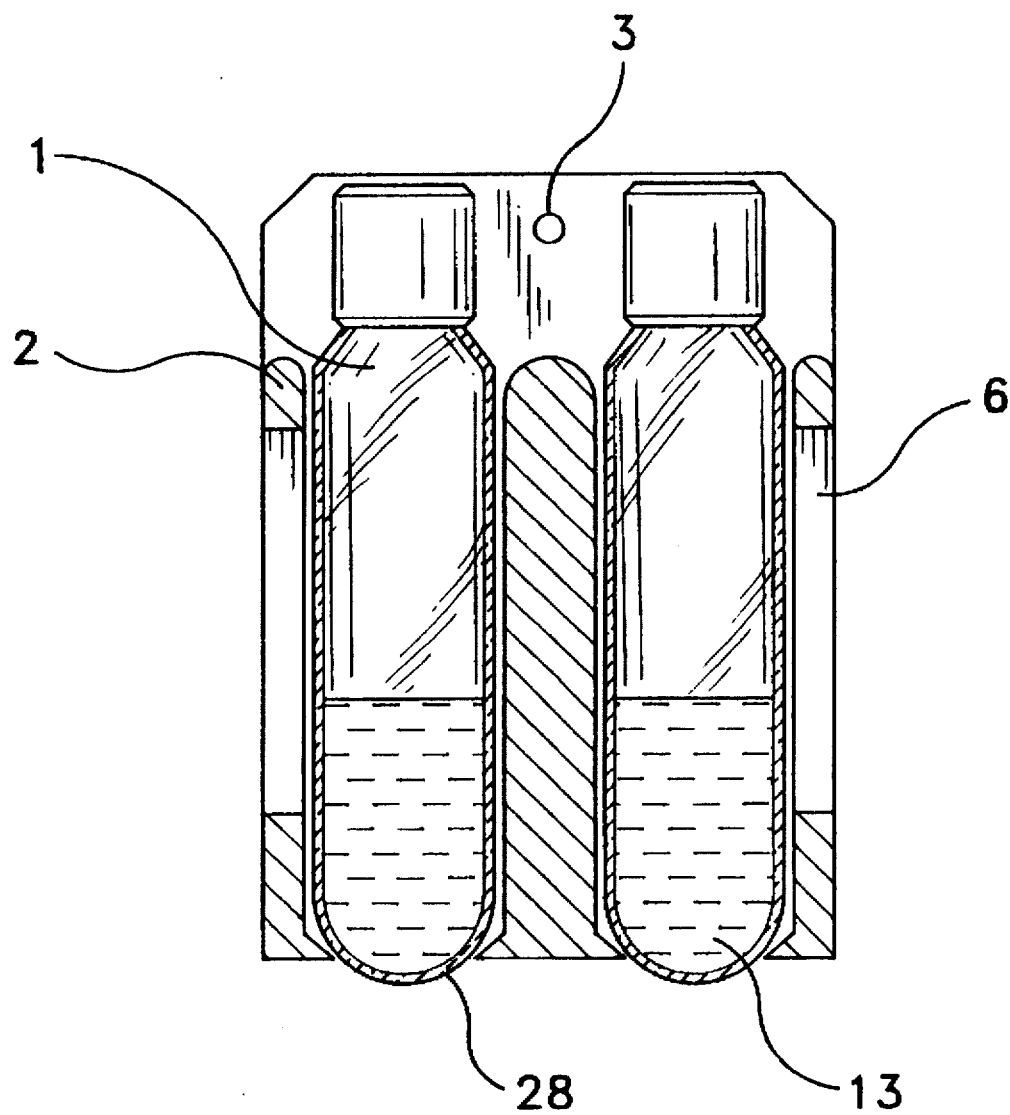
FIG. 2 shows a cross-sectional view of a vessel with one sample tube in each row.
Figure 3:
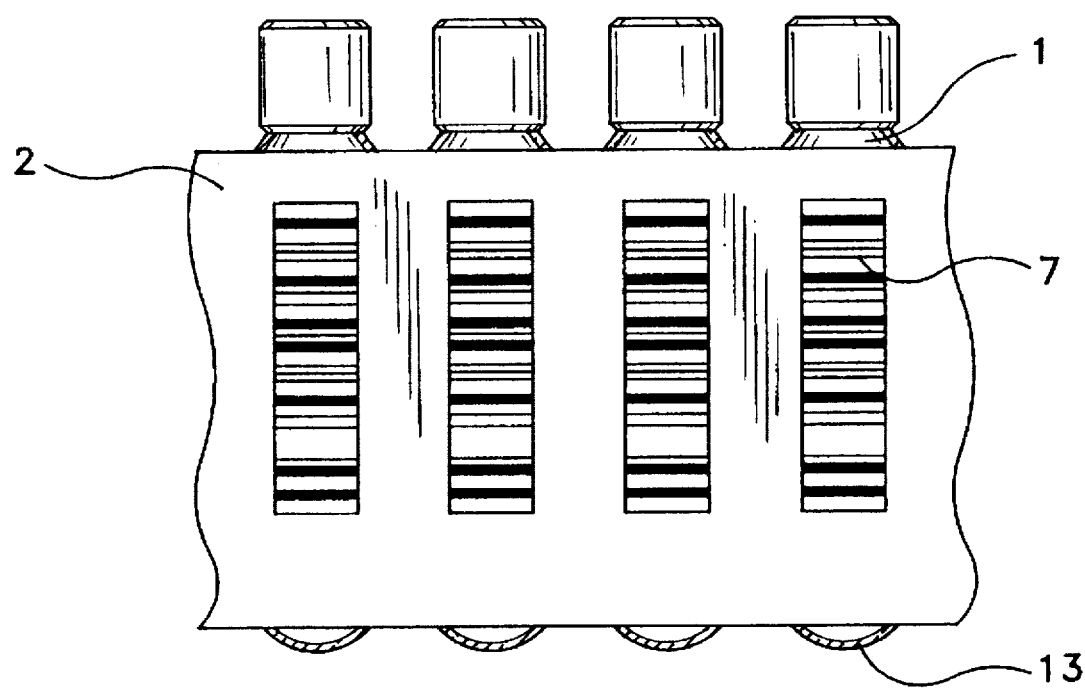
FIG. 3 shows a section of a long vessel with windows to access barcode labels attached to each sample tube.

Vessels 2 accommodate two rows of sample tubes 1 as illustrated in FIGS. 2 and 3. In the long vessel walls, there are windows 6 that allow access to barcode labels 7 attached to each sample tube 1. As shown in FIGS. 1 and 4, two barcode readers 8 and 9 are arranged on a carriage 10 that can be moved parallel to spool shaft 5 on rails 11 mounted to the apparatus housing 12 below spool 4. For barcode reading, the spool rotation is interrupted and carriage 10 is moved across the length of spool 4. In this way, two rows of sample tubes 1 are barcode-scanned. In a next step, spool 4 is rotated by an appropriate angle so that the next two vessels can be scanned. Carriage 10 is moved again across the whole spool length of spool 4. This procedure is repeated until all sample tubes 1 are scanned.

Within the vessel bottoms, there are two rows of openings 28 to allow for interrogating bacterial sensors 13 that are attached to the inner bottom of each sample tube 1, as shown in FIGS. 2 and 3. A sensor reading head 14 is mounted to the same carriage 10 that holds the two barcode readers 8 and 9 (see FIGS. 1 and 4). The sensor reading head 14 is constructed so that it can access two adjacent sample tubes 1, i.e., one in each row, simultaneously. As mentioned above, in order to interrogate a particular vessel 2, spool 4 is rotated into the appropriate angular position and carriage 10 is moved across the length of spool 4. This procedure is repeated until the sample tubes in all vessels within the apparatus are read.

Figure 8:
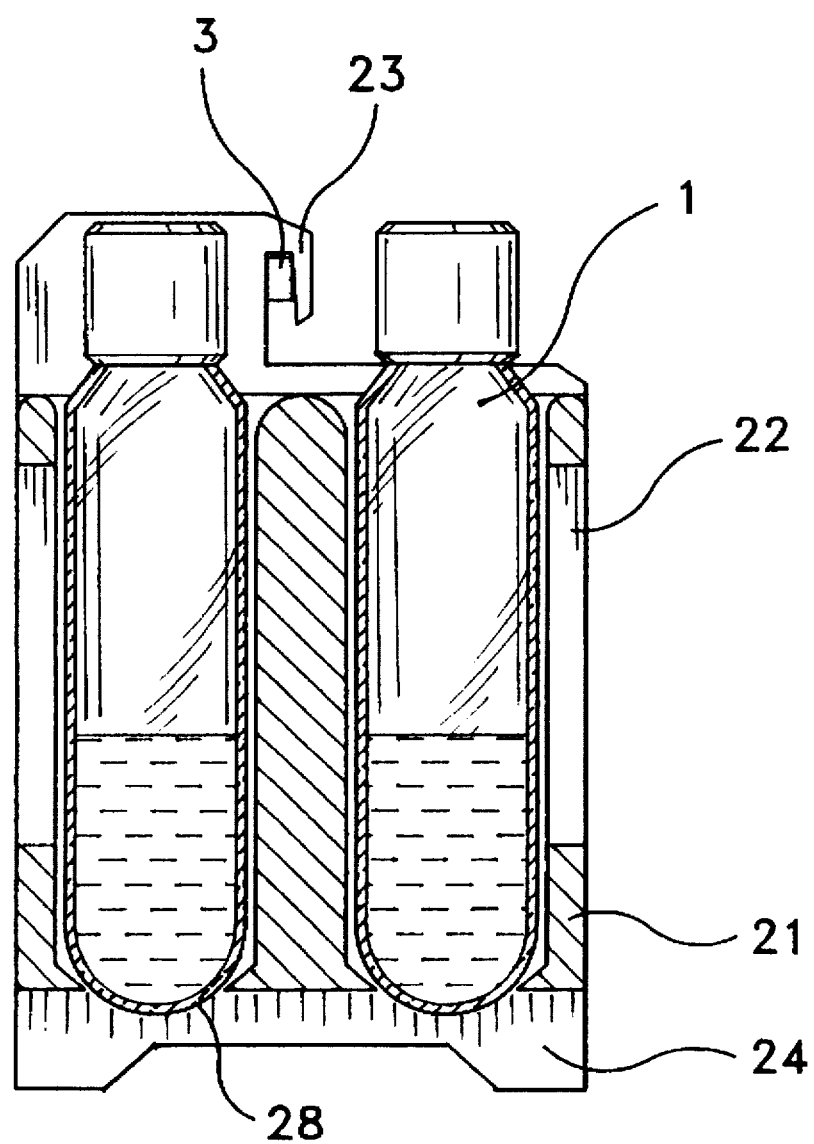
FIG. 8 shows a cross-sectional view of a segmented vessel that can be removed from the rods and re-inserted after loading a new group of test samples.
Figure 9:
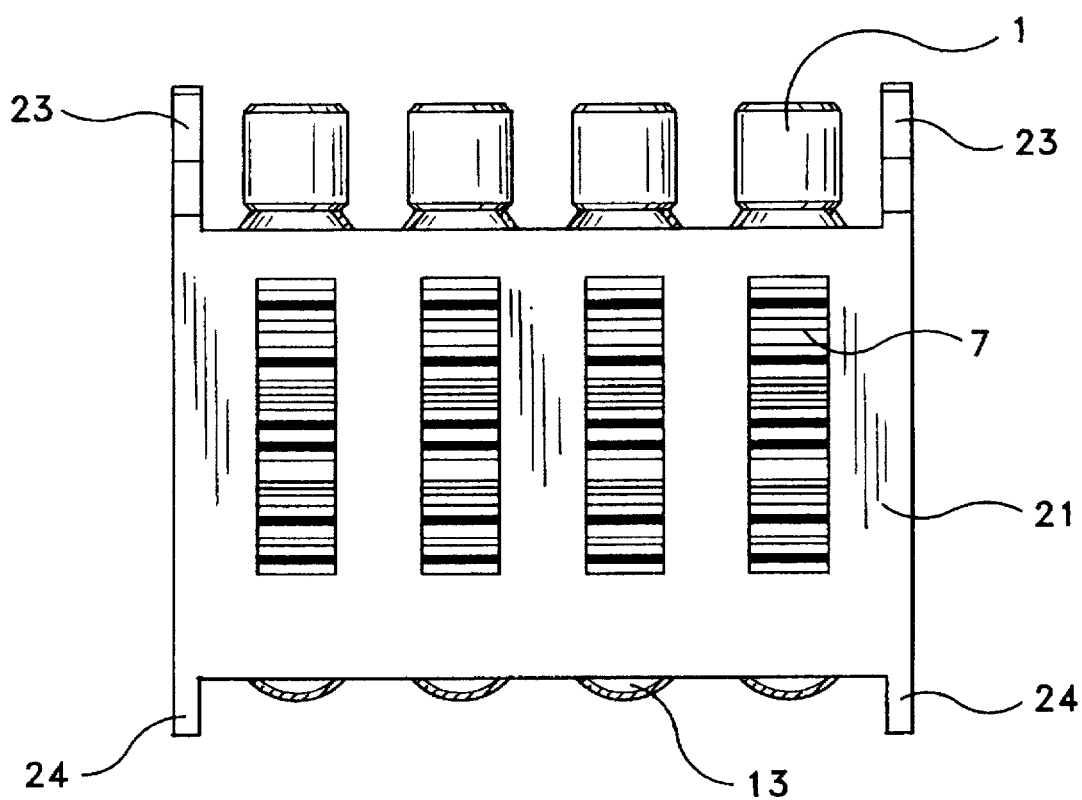
FIG. 9 shows a segmented vessel with windows to access barcode labels attached to each sample tube.

Vessels 2 can be as long as spool 4 and can be mounted permanently to the horizontal rods 3. However, it is also possible to segment vessels 2 into appropriate lengths so that the number of sample tubes 1 within one vessel 2 matches with particular requirements for antimicrobial susceptibility testing (AST). In this case, it may be more convenient if the vessels can be removed from rods 3, and re-inserted after loading a new group of test samples. This feature of the invention is illustrated in FIGS. 8 and 9. The short vessel 21 has windows 22 to allow for the reading of barcodes 7 that are attached to sample tubes 1. At both ends of each vessel 21 there are hooks 23 allowing vessels 21 to hang from horizontal rod 3, which has a rectangular cross-section in this case. Also at both ends of each vessel 21 there are legs 24 that provide a stable positioning of vessels 21 on a bench during loading and unloading of sample tubes 1.

Figure 10:
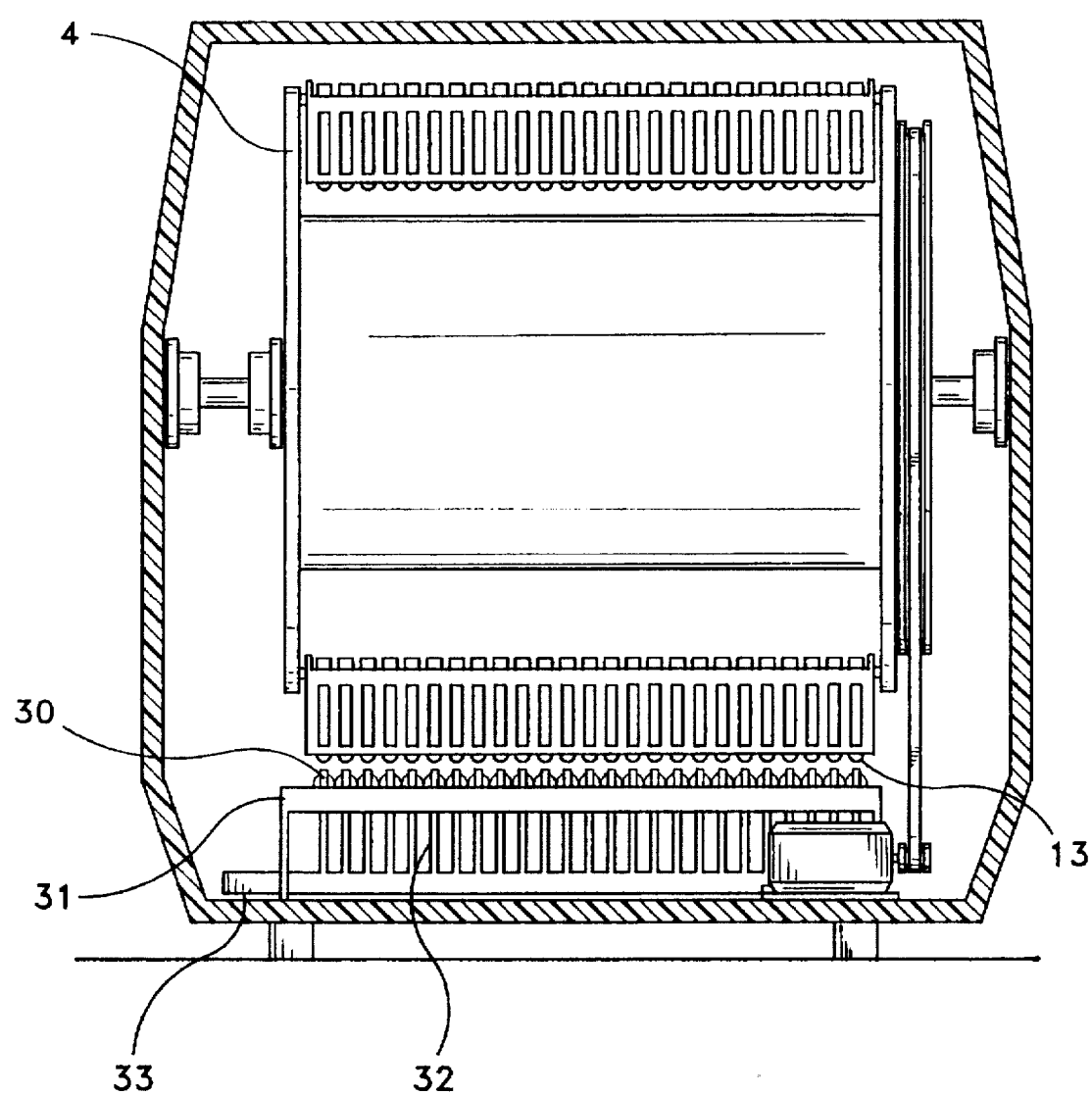
FIG. 10 shows a side view of the interior of an alternative compact high-volume microorganism detection apparatus.

A modification of an apparatus according to the invention is illustrated in FIG. 10. This apparatus version does not contain rails and does not contain a carriage with a sensor reading head and/or barcode reader. Instead, a series of light-emitting diodes (LED's) 30 is mounted onto a platform 31 with the number of LED's being equal to the number of sample tubes 1 per row. Adjacent to each of the LED's 30, one end of an optical fiber 32 is mounted to the platform. The other ends of all fibers 32 are arranged closely together, forming an end of a fiber-optic bundle 33, which is arranged in front of a large-size photodetector such as a conventional photomultiplier (not shown in FIG. 10).

In operation, a first LED 30 is turned on, and the light re-emitted by the chemical sensor 13 in the corresponding sample tube is collected by the adjacent optical fiber 32. This light is then fed to the photodetector and the electrical signal is measured. Next, the first LED is turned off and a second LED is switched on, with the corresponding sensor light being monitored using the same photodetector. Due to the fact that the system "knows" which LED has been activated, it also knows which sample tube is emitting sensor light. After all sample tubes within a row have been interrogated, spool 4 is rotated until another row of sample tubes can be interrogated.

In the apparatus just described, no barcode reading is performed within the instrument. Instead, the step of barcode reading is accomplished manually. This provides an increase in the number of rows per vessel beyond two, which results in an increased packaging density. As an example, 864 MGIT tubes are accommodated in the space which is available within a standard BACTEC™ 9120 blood culture instrument, currently manufactured by Becton Dickinson and Company, Sparks, Md.

The advantage of the apparatus shown in FIG. 10 and described here is that no mechanically moving carriage and no flexible electric cables are required to interrogate the numerous sample tubes. Therefore, extreme high reliability can be accomplished for the whole instrument. Moreover, due to the fact that a series of LED's is used, burn-out of one LED does not disable the whole instrument.

The present invention is not limited to the field of tuberculosis detection. The invention can also be applied, for instance, to detecting the presence of bacteria in blood culture bottles. An embodiment of this kind is depicted schematically in FIG. 11. Here, a cylindrical spool 104 rotating around a horizontal shaft 105 is mounted inside a thermo-isolated housing 112. A multitude of blood culture bottles 101 are oriented side by side in a number of long vessels 102 that are hanging vertically on horizontal rods 103 mounted to the circumference of spool 104. Within vessels 102, blood culture bottles 101 are oriented in a horizontal orientation. After opening a door 120 in the front wall of housing 112, blood culture bottles can be loaded or unloaded.

During rotation of spool 104, vessels 102 remain vertically oriented. In this way, any sample agitation can be avoided, if required for biological reasons. Inside of housing 112 there is arranged a member 142 that can be positioned close to vessels 102 by a positioning device 141. If positioning device 141 is activated then member 142 will touch a protrusion 140 on vessels 102. In this way, each vessel 102 and therefore each blood culture bottle 101 will be agitated when it passes by member 142. The degree of agitation can be controlled via positioning device 141.

Figure 11:
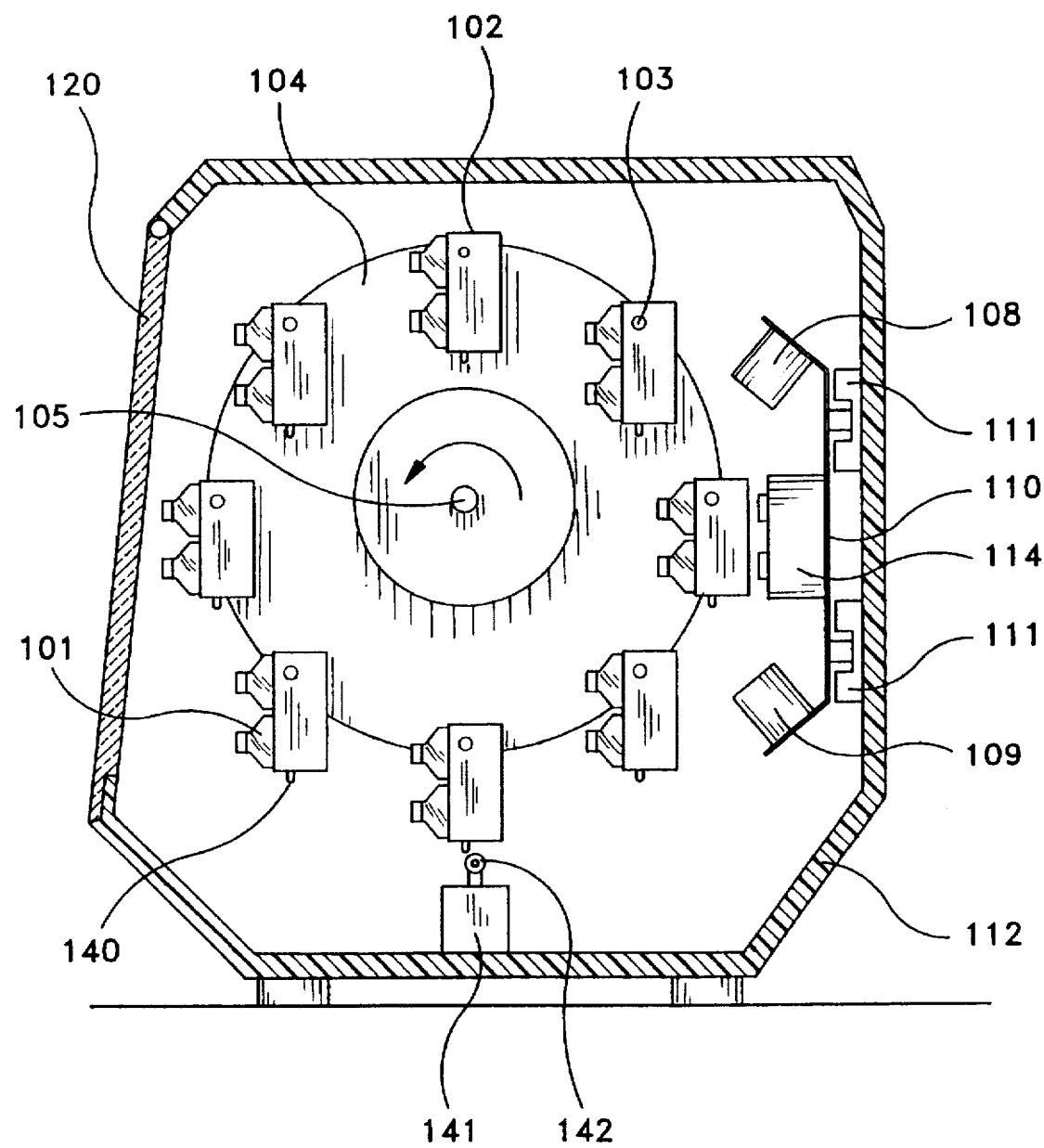
FIGS. 11 and 12 show a side view of the interior of yet other compact high-volume microorganism detection apparatus having modified orientations.

The presence of bacteria in blood culture bottles is detected by means of conventional chemical fluorescent or colorimetric sensors that are disposed to the inner bottom of each blood culture bottle 101. In the embodiment depicted in FIG. 11, these sensors and the barcode labels attached to each blood culture bottle are read out in the same way as described in connection with the embodiment of FIG. 1. The vessels 102 accommodate two rows of blood culture bottles 101. In the long vessel walls, there are windows that allow access to barcode labels on each bottle 101. Within the vessel bottoms, there are also two rows of openings to allow for interrogating the bacterial sensors that are attached to the inner bottom of each bottle 101. As shown in FIG. 11, two barcode readers 108 and 109 are arranged on a carriage 110 that can be moved parallel to spool shaft 105 on rails 111 mounted to the apparatus housing 112 behind spool 104. For barcode reading, spool rotation is interrupted and carriage 110 is moved across the whole length of spool 104. In this way, two rows of blood culture bottles 101 are barcode scanned. In a next step, spool 104 is rotated by an appropriate angle so that the next two vessels can be scanned by moving carriage 110 across the whole spool length. This procedure is repeated until all blood culture bottles 101 are scanned.

To read out the sensors in bottles 101, a sensor reading head 114 is mounted to the same carriage 110 that holds the two barcode readers 108 and 109 (see FIG. 11). Sensor reading head 114 is constructed so that it can access two adjacent blood culture bottles 101, i.e., one in each row, simultaneously. As mentioned above, in order to interrogate vessels 102 spool 104 is rotated into the appropriate angular position and carriage 110 is moved across the whole spool length. This procedure is repeated until the blood culture bottles 101 in all vessels within the apparatus are read.

It is also possible to modify the blood culture apparatus shown in FIG. 11 so that no moving sensor head is present. In other words, it is possible to read the blood culture apparatus of FIG. 11 with an array of LED's and optical fibers as illustrated in the embodiment of FIG. 10. Again, the advantage of this apparatus version would be that no mechanically moving carriage and no flexible electric cables are required to interrogate the many blood culture bottles. Therefore, high reliability and low production cost can be accomplished for the whole instrument.

It would be still within the spirit of the invention if the vessels are designed so that the sample tubes or the blood culture bottles are hanging in an intermediate orientation, i.e., in between the two limiting cases of vertical orientation or horizontal orientation. A typical case would be represented by a 45-degree orientation. This option offers both, optimum access to the sample containers during loading and unloading, and prevention of potential spills in case of a leakage in the rubber septum. Moreover, in the 45-degree-like orientation, the chemical sensor is in direct contact with the liquid most of the time. This may not be the case for a strictly horizontal bottle orientation.

Figure 12:
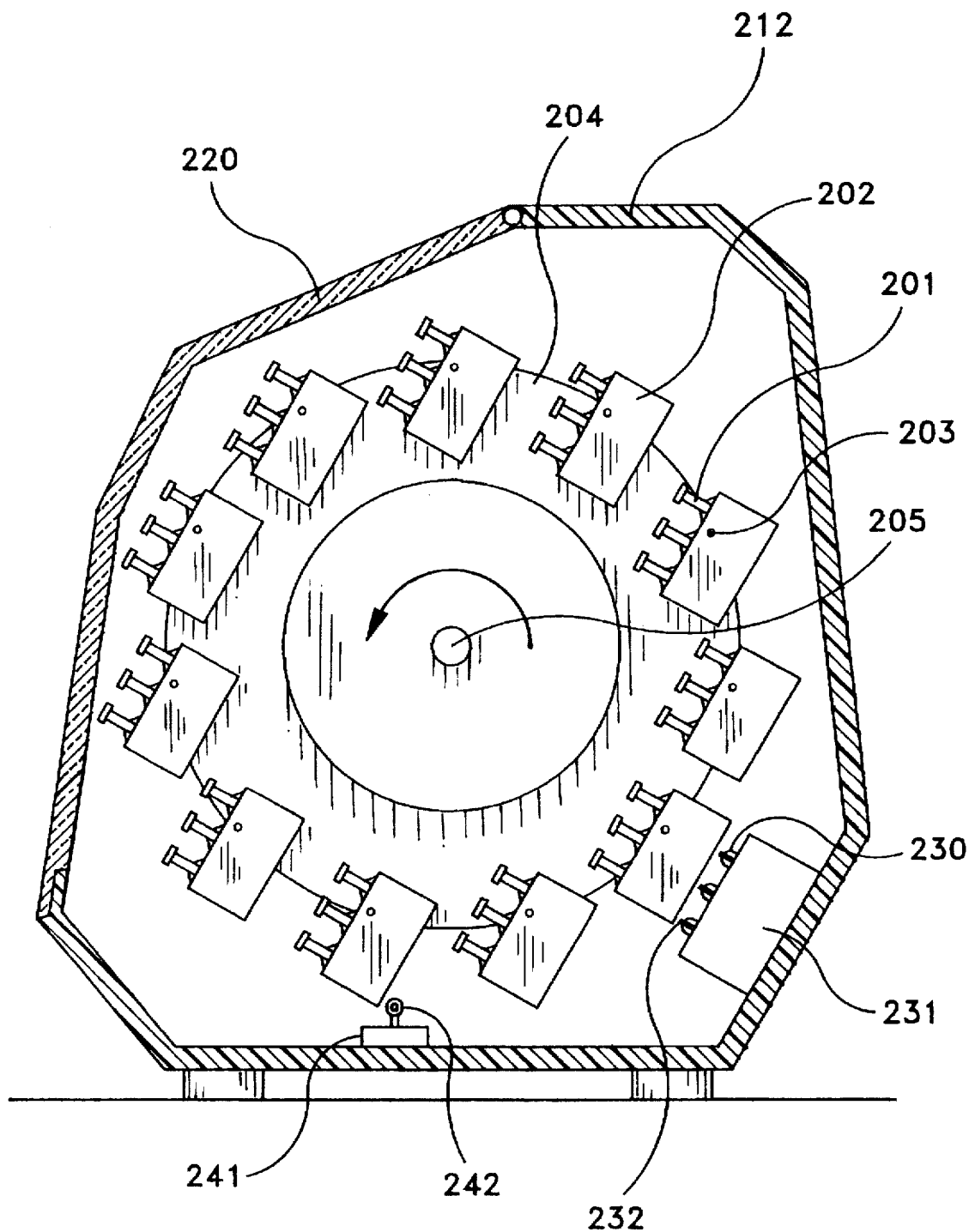

An embodiment of this kind is depicted schematically in FIG. 12. Here again, a cylindrical spool 204 rotating around a horizontal shaft 205 is mounted inside a thermo-isolated housing 212. A multitude of blood culture bottles 201 is oriented side by side in a number of long vessels 202 that are handing in a 45-degree orientation on horizontal rods 203 mounted to the circumference of a spool 204. Within vessels 202, blood culture bottles 201 are oriented in a 45-degree orientation. After opening a door 220 in the front wall of housing 212, blood culture bottles 201 can be loaded or unloaded.

During rotation of spool 204, vessels 202 remain in their 45-degree orientation. In this way, any sample agitation can be avoided, if required for biological reasons. Inside of housing 212 there is arranged a member 242 that can be positioned dose to vessels 202 by a positioning device 241. If positioning device 241 is activated then member 242 will touch vessels 202. In this way, each vessel 202 and, therefore, each blood culture bottle 201 will be agitated when it passes by member 242. The degree of agitation can be controlled via positioning device 241.

The blood culture apparatus shown in FIG. 12 has a similar fluorescence reading system as the apparatus depicted in FIG. 10, which comprises an array of LED's 230 and optical fibers 232 that are mounted to a platform 231. Again, the advantage of this apparatus version would be the fact that no mechanically moving carriage and no flexible electric cables are required to interrogate the many blood culture bottles. Therefore, extreme high reliability and low production cost can be accomplished for the whole instrument.

What is claimed is:

1. A compact microorganism detection apparatus comprising:
   a plurality of sample tubes each having a sample suspected to contain a microorganism;
   a plurality of vessels including a plurality of chambers in a top surface for receiving said sample tubes;
   a spool rotatable about a horizontal axis having a plurality of rods mounted to the circumference of said spool, wherein each of said plurality of rods receives one of said plurality of vessels such that said vessel hangs in a vertical orientation;
   a mechanism for rotating said spool about said axis; and
   means for detecting microorganisms within each sample tube in each of said plurality of vessels.

2. A compact microorganism detection apparatus according to claim 1, wherein each of said vessels includes a matrix of said chambers including a plurality of rows and a plurality of columns, wherein each chamber receives one of said sample tubes.

3. A compact microorganism detection apparatus according to claim 1, further comprising means for moving said detecting means across the length of one of said plurality of vessels to detect microorganisms in each sample tube in said vessel.

4. A compact microorganism detection apparatus according to claim 3, wherein said means for moving said detecting means comprises:
   a pair of rails mounted parallel to said horizontal axis and adjacent the circumference of said spool; and
   a carriage for carrying said detecting means, said carriage mounted for movement across the length of said spool on said pair of rails.

5. A compact microorganism detection apparatus according to claim 1, further comprising means for identifying each sample tube in each of said vessels.

6. A compact microorganism detection apparatus according to claim 5, wherein each sample tube further comprises an independent and distinct barcode label, each chamber includes a window through which said barcode label can be viewed from outside said vessel, and said means for identifying each sample tube comprises a barcode reader.

7. A compact microorganism detection apparatus according to claim 6, means for moving said barcode reader and said detecting means across the length of one of said plurality of vessels to scan said barcode labels and detect microorganisms in each sample tube in said vessel, respectively.

8. A compact microorganism detection apparatus according to claim 7, wherein said means for moving said barcode reader and said detecting means comprises:
   a pair of rails mounted parallel to said horizontal axis and adjacent the circumference of said spool; and
   a carriage for carrying said barcode reader and said detecting means, said carriage mounted for movement across the length of said spool on said pair of rails.

9. A compact microorganism detection apparatus according to claim 1, further comprising means for agitating one or more of said plurality of vessels by rocking said vessel as said spool is rotated by said rotating mechanism.

10. A compact microorganism detection apparatus according to claim 9, wherein said agitating means is comprised of:
    a metallic disk on one end of said rod;
    an electro-magnet mounted on said spool near adjacent to said metallic disk;
    a brush extending from said electro-magnet away from said spool; and
    a segmented electrode array mounted adjacent said spool such that:
    (i) when said brush makes contact with a segment of said segmented electrode array as said spool is rotated said electro-magnet receives electrical power via said brush which locks said metallic disk to said spool and causes said vessel to be tilted during further rotation of said spool, and
    (ii) when said brush does not make contact with the segment, said electromagnet does not receive electrical power, is deactivated and causes said vessel to fall back into the vertical orientation and stops agitating.

11. A compact microorganism detection apparatus according to claim 9, wherein said agitating means is comprised of:
    a protrusion on each of said vessels; and
    a member adjacent said spool that is movable into and out of a position close to one of said vessels as said vessels rotate on said spool, wherein:
    (i) when said member is in the position it makes contact with said protrusion on said vessel and causes said vessel to agitate in a rocking motion, and
    (ii) when said member is out of the position said vessel falls back into the vertical orientation and stops agitating.

12. A compact microorganism detection apparatus according to claim 1, wherein said means for detecting microorganisms within each sample tube in each of said plurality of vessels comprises:

a platform mounted adjacent to the circumference of said spool;

a plurality of light-emitting diodes mounted on said platform such that each sample tube in said plurality of vessels passes by one of said plurality of light-emitting diodes when said spool is rotating about said axis;

a plurality of optical fibers mounted to said platform, wherein each of said plurality of optical fibers is adjacent to a respective one of said plurality of light-emitting diodes; and a photodetector located at the other end of each optical fiber for monitoring each of said plurality of optical fibers and generating an electrical signal corresponding to light being received by said photodetector to detect microorganisms within each sample tube in each of said plurality of vessels.

* * * * *